United States Patent
Lotz et al.

(10) Patent No.: US 7,450,233 B2
(45) Date of Patent: Nov. 11, 2008

(54) MEASURING DEVICE FOR THE MEASUREMENT OF OPTICAL PROPERTIES OF COATED SUBSTRATES

(75) Inventors: Hans-Georg Lotz, Grundau-Rothenbergen (DE); Peter Sauer, Schluchtern (DE); Stefan Hein, Blankenbach (DE); Peter Skuk, Nidderau (DE)

(73) Assignee: Applied Materials GmbH & Co. KG, Alzenau (DE)

( * ) Notice: Subject to any disclaimer, the term of this patent is extended or adjusted under 35 U.S.C. 154(b) by 916 days.

(21) Appl. No.: 10/996,808

(22) Filed: Nov. 24, 2004

(65) Prior Publication Data

US 2006/0192964 A1     Aug. 31, 2006

(30) Foreign Application Priority Data

May 22, 2004    (EP)    ................................. 04012165

(51) Int. Cl.
*G01N 21/84* (2006.01)
*C23C 14/54* (2006.01)

(52) U.S. Cl. .................. 356/429; 356/630; 204/192.13; 204/192.26; 204/192.29; 204/298.03; 427/10; 118/712

(58) Field of Classification Search ......... 356/429–431, 356/445–448, 630–632; 204/192.13, 192.26, 204/192.29, 298.03, 298.26; 118/712, 719, 118/730, 664–665; 427/8, 10, 126.3, 126.4; 438/7, 61, 907

See application file for complete search history.

(56) References Cited

U.S. PATENT DOCUMENTS

| | | | |
|---|---|---|---|
| 2,773,412 A * | 12/1956 | Huck | ........................ 356/632 |
| 2,810,663 A | 10/1957 | Reynolds et al. | |
| 3,496,359 A * | 2/1970 | Weinstock et al. | ....... 250/358.1 |
| 4,669,873 A | 6/1987 | Wirz | |
| 4,693,803 A | 9/1987 | Casey et al. | |
| 5,154,810 A * | 10/1992 | Kamerling et al. | ..... 204/192.13 |
| 5,277,928 A * | 1/1994 | Strandberg | ................... 427/10 |
| 5,527,396 A * | 6/1996 | Saitoh et al. | .......... 118/723 MP |
| 5,772,861 A * | 6/1998 | Meredith et al. | ....... 204/298.03 |
| 6,231,732 B1 * | 5/2001 | Hollars et al. | .......... 204/298.26 |
| 6,549,291 B1 * | 4/2003 | Dieter et al. | ................. 356/630 |
| 6,863,785 B2 * | 3/2005 | Shidoji et al. | .......... 204/192.13 |

FOREIGN PATENT DOCUMENTS

| | | |
|---|---|---|
| DE | 922 596 C | 1/1955 |
| DE | 22 25 946 A | 12/1973 |
| DE | 34 06 645 C2 | 8/1985 |
| DE | 100 19 258 C1 | 11/2001 |
| JP | 9136323 | 5/1997 |
| RU | 2087861 C1 | 8/1997 |
| SU | 952373 | 8/1982 |

* cited by examiner

*Primary Examiner*—Hoa Q Pham
(74) *Attorney, Agent, or Firm*—Fulbright & Jaworski L.L.P.

(57) ABSTRACT

A measuring device includes several sequentially disposed coating chambers for measuring optical properties of coated substrates. These coating chambers are separated from one another by partitioning walls, whose free ends are located closely above the substrate. The substrate is preferably a continuous film. By measuring the reflection, the transmission, etc. of the substrate between the individual coating chambers, it becomes possible to carry out measurements within only partially completed layer systems. This yields advantages for the technical operation control of the coating process.

12 Claims, 2 Drawing Sheets

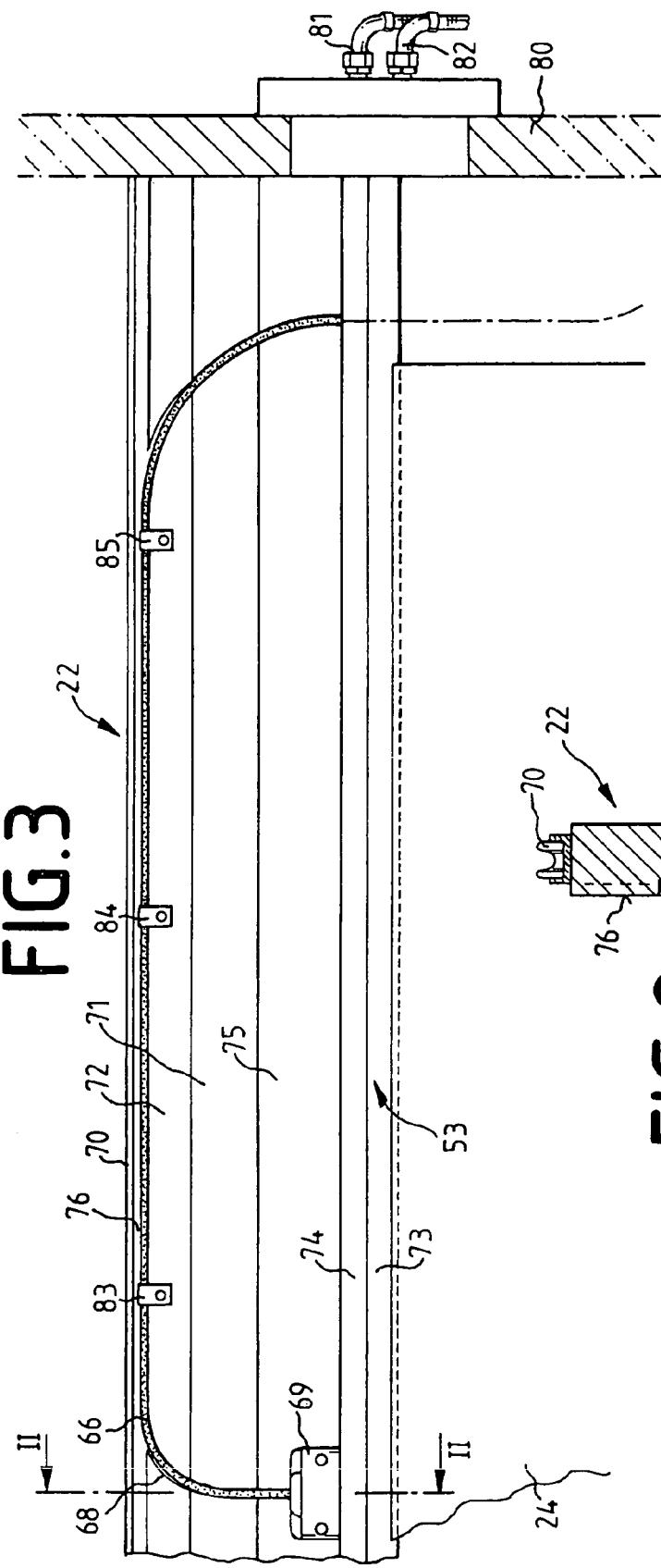
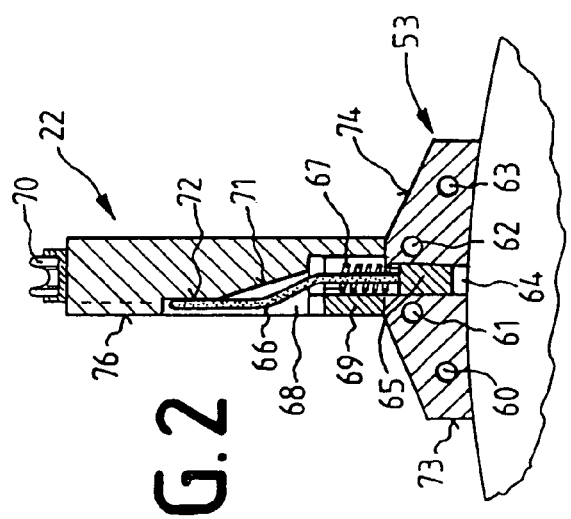

US 7,450,233 B2

MEASURING DEVICE FOR THE MEASUREMENT OF OPTICAL PROPERTIES OF COATED SUBSTRATES

BACKGROUND AND SUMMARY OF THE INVENTION

This application claims priority from European Patent Application No. 04 012 165.9 filed May 22, 2004, hereby incorporated by reference in its entirety.

Coated substrates, for example coated architectural glasses or coated synthetic films, have altered optical properties after their coating. Whether or not these optical properties meet the desired properties can be determined by the corresponding measurements. Subsequent determination of the optical properties, i.e. after one or several layers have already been deposited on the substrate, at that point can only serve for the purpose of separating good coatings from the poor ones. The intent is therefore of acquiring, if possible, the optical properties already during the coating process in order to intervene in the coating process itself if necessary.

A spectrophotometer configuration is already known with which, while maintaining measuring accuracy with a single measuring and evaluating system, a relatively large number of measuring objects can be acquired within a closed chamber (DE 34 06 645 C2). Herein several measuring sites, which are disposed in a closed chamber, are connected through several fiber optic cables into a light resolving system. Through an associated movable diaphragm virtually any desired number of measuring sites or measuring objects can be acquired with this single light resolving system and the measuring results obtained here can be evaluated.

However, this photometer configuration is not suitable for the in-line measurement of substrates to be coated, which pass through several chambers.

A device is furthermore known for the production of coated transmission lines, in which a cable core is sequentially passed through four different types of chambers (DE 922 596). These are a metal vaporization chamber, metal layer thickness control chamber, insulation material vaporization chamber and insulation layer thickness control chamber. The control chambers serve for determining the thickness of a dielectric layer. Therein a control signal is generated through a directional light beam, which is emitted by a suitable light source and, via an optical system, is incident on the dielectric layer. The beam reflected from this layer is directed via a suitable optical system onto a photoelectric cell. The measuring device comprised of light source, optical system and photoelectric system is here distributed over an entire chamber.

In another known method for vacuum coating web-form transparent substrates, a substrate is coated at least once with a reflection layer and subsequently with at least one transparent layer (DE 100 19 258 C1). During or after the coating with the transparent layer, reflected light is measured in order to obtain information about the transparent layer, with the aid of which process parameters are adapted and/or layer parameters are controlled. The measuring device for the reflected light is located outside of a coating chamber and is disposed opposite the web-form substrate.

The invention, consequently, addresses the problem of measuring in coating installations comprised of several chambers the optical properties of coated substrates even during the coating process itself.

This problem is solved according to present invention.

The invention thus relates to a measuring device, which comprises several sequential coating chambers, for measuring optical properties of coated substrates. These coating chambers are separated from one another by partitioning walls, whose free end is disposed closely above the substrate. The substrate is preferably a continuous film. By measuring the reflection, the transmission, etc. of the substrate between the individual coating chambers, it is possible to carry out measurements within only partially completed layer systems. This yields advantages for the technical operation control of the coating process.

The advantage attained with the invention comprises in particular improving the process control. It is possible in complex optical layer systems to measure the reflection of a partial layer system after the first, second, third, etc. layer. This permits drawing direct conclusions regarding the quality of the layer thickness of the layer applied up to the time of measurement.

An embodiment example of the invention is depicted in the drawing and will be described in further detail in the following.

BRIEF DESCRIPTION OF THE DRAWINGS

FIG. 2 shows section through a partitioning wall in which a measuring head is disposed, FIG. 3 shows an optical waveguide laid out in a partitioning wall.

DETAILED DESCRIPTION

Figure 1:
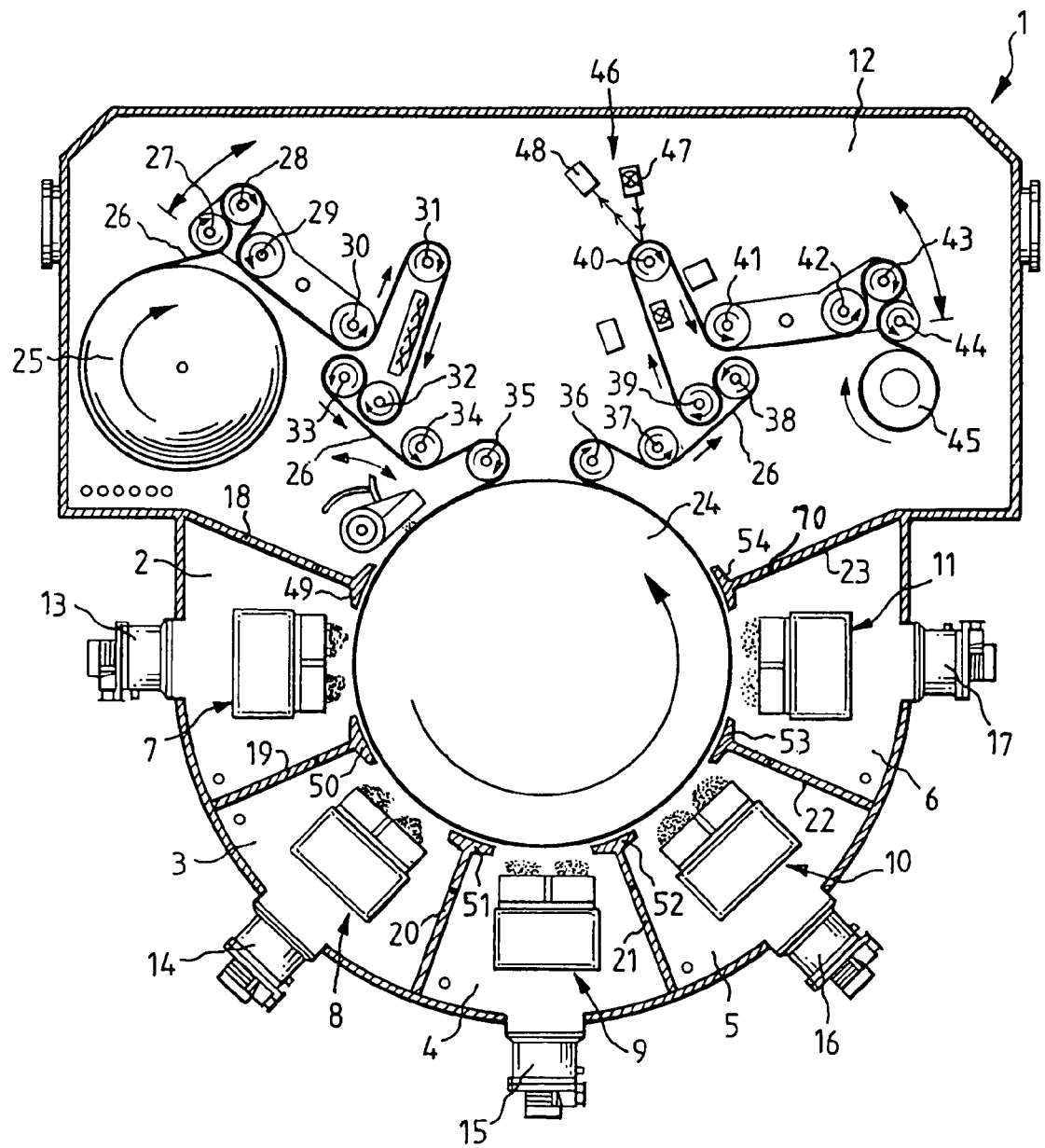
FIG. 1 shows sectional view from the side onto a coating installation for webs or films.

FIG. 1 shows a coating configuration 1 for webs or films. This coating configuration 1 comprises several coating chambers 2, 3, 4, 5, 6, in each of which is located a sputter device 7, 8, 9, 10, 11. Apart from the coating chambers 2 to 6, the coating installation 1 also comprises a feed-out and wind-up chamber 12. Each coating chamber 2 to 6 is provided with a pump 13 to 17, which generates a vacuum in the coating chambers 2 to 6. Between the individual coating chambers 2 to 6 and toward the feed-out and wind-up chambers 12 partitioning walls 18 to 23 are provided, which terminate closely in front of a coating drum 24. The axis of rotation of the coating drum 24 leads into the plane of drawing, i.e. the feed-out and wind-up chambers are located above, while the coating chambers 2 to 6 are disposed below.

In the feed-out and wind-up chamber 12 is located a roll 25, from which a film 26 to be coated is wound out. This film is guided over several small tension and guide rollers 27 to 35 to the surface of the coating drum 24. After the film 26 has circled around the coating drum 24, it is wound up via several rollers 36 to 44 onto a wind-up roll 45. In the proximity of roller 40 is disposed a reflection measuring instrument 46 containing a light source 47 and a sensor 48.

The partitioning walls 18 to 23 are provided in the proximity of the coating drum 24 with a broadened out foot 49 to 54, whose outer contour is adapted to the circular contour of the coating drum 24. In each of these feet 49 to 54 is disposed a reflection measuring head, not shown in FIG. 1.

When the film 26 is moved about the coating drum 24, it can be provided in each coating chamber 2 to 6 with a differential layer preferably applied by sputtering. The optical properties of the uncoated or coated film 26 can consequently be measured at each transition from one chamber to the next.

FIG. 2 shows in detail the foot 53 of the partitioning wall 22. It is evident that foot 53 has several bores 60 to 63, through which a cooling medium can flow. In addition, in the center of foot 53 a bore 64 is provided, in which is disposed a reflection measuring head 65. This reflection measuring head 65 contains a reflection measuring instrument, which corresponds essentially to the reflection measuring instrument 46 according to FIG. 1. However, it is connected with a harness of cables 66 about the lower region of which a helical spring 67 is wound. In the partitioning wall 22 is provided a lateral recess 68, in which runs the harness of cables 66. The harness of cables 66 contains two fiber optic bundles. The one fiber optic bundle serves for supplying light onto the coated substrate, while the other collects the reflected light. The collected light is projected onto a receiver disposed outside of the installation, which generates an electric signal conducted to a central evaluation site.

Adjoining an oblique face 71 is a perpendicular face 72. A seal 70 closes off the lower portion of the partitioning wall 22.

FIG. 3 depicts a view perpendicular to the representation of FIGS. 1 and 2.

The coating drum 24 or its rotational axis extends in the horizontal direction. Above the coating drum 24 is located the foot 53 with its vertically extending side portion 73 and the adjoining portion 74 extending obliquely. On this foot 53 is supported a housing 69 of the reflection measuring head 65. The harness of cables 66 runs initially in recess 68 and is subsequently guided parallel to the seal 70 and is subsequently carried through an outer chamber wall 80 to the outside. In this outer chamber wall are cooling water inlets and outlets. The harness of cables 66 is fastened by means of retainers 83, 84, 85 in the upper region of the partitioning wall 22.

The invention claimed is:

1. A measuring device for the measurement of optical properties of coated substrates in an installation said installation comprising several sequentially disposed coating chambers disposed one after the other, and partitioning walls are provided between the coating chambers, whose free end is disposed closely above the substrate, and the substrate is transported from one chamber into the next, wherein the measuring device is provided at the free end of the partitioning walls.

2. A measuring device as claimed in claim 1, wherein it is integrated into the free end of the partitioning walls.

3. A measuring device as claimed in claim 1, wherein the optical properties are the reflections.

4. A measuring device as claimed in claim 1, wherein it includes a reflection measuring head.

5. A measuring device as claimed in claim 4, wherein the reflection measuring head is connected with a harness of cables, which includes two fiber optic bundles.

6. A measuring device as claimed in claim 5, wherein the harness of cables is guided along the partitioning wall.

7. A measuring device as claimed in claim 6, wherein the harness of cables is brought out of the coating chamber and supplied via an optoelectric converter to an evaluation unit.

8. A measuring device as claimed in claim 1, wherein the installation comprises a wind-up and feed-out chamber and several coating chambers.

9. A measuring device as claimed in claim 1, wherein the installation comprises a coating drum, disposed between the wind-up and feed-out chamber and the coating chambers.

10. A measuring device as claimed in claim 9, wherein the coating chambers are disposed circularly around the coating drum.

11. A measuring device as claimed in claim 1 wherein the substrate is a flexible film.

12. A measuring device as claimed in claim 1, wherein in the feed-out and wind-up chamber a further optical measuring unit is provided.

* * * * *